(12) United States Patent
Meyer et al.

(10) Patent No.: US 6,731,972 B2
(45) Date of Patent: May 4, 2004

(54) EVALUATION METHOD AND APPARATUS FOR DETERMINING THE TIME STATIONARITY OF MEASURED PHYSIOLOGICAL SIGNALS

(75) Inventors: Wolfgang Meyer, Erlangen (DE); Max Schaldach, deceased, late of Erlangen (DE); Max Schaldach, Jr., legal representative, Berlin (DE)

(73) Assignee: Biotronik Mess- und Therapiegeräte GmbH & Co. Ingenieurbüro Berlin, Berlin (DE)

( * ) Notice: Subject to any disclaimer, the term of this patent is extended or adjusted under 35 U.S.C. 154(b) by 219 days.

(21) Appl. No.: 09/912,421

(22) Filed: Jul. 26, 2001

(65) Prior Publication Data

US 2002/0072772 A1 Jun. 13, 2002

(30) Foreign Application Priority Data

Jul. 28, 2000 (DE) .......................... 100 36 842

(51) Int. Cl.$^7$ ............................................. A61B 5/0402
(52) U.S. Cl. ...................... 600/509; 600/300; 600/519; 600/521; 128/920
(58) Field of Search ................................ 600/509, 300, 600/515, 519, 521; 128/920, 923

(56) References Cited

U.S. PATENT DOCUMENTS

| | | | |
|---|---|---|---|
| 5,353,801 A | * 10/1994 | Hoegnelid | 600/508 |
| 5,842,997 A | 12/1998 | Verrier et al. | |
| 6,091,990 A | 7/2000 | Hsu et al. | |
| 6,144,877 A | * 11/2000 | DePetrillo | 600/515 |

FOREIGN PATENT DOCUMENTS

| | | |
|---|---|---|
| DE | 199 38 376 A1 | 6/1999 |
| DE | 199 30 598 A1 | 7/2000 |
| EP | 0 958 843 A1 | 11/1999 |
| GB | 2 227 842 A | 8/1990 |
| WO | WO 97/33238 A1 | 9/1997 |

OTHER PUBLICATIONS

Glass et al., *Time series analysis of complex dynamics in physiology and medicine*, Medical Progress through technology, vol. 19, No. 3, pp. 115–128, 1993.

Zhang et al. "Detecting Ventricular Tachycardia and Fibrillation by Complexity Measure," IEEE Transactions on Biomedical Engineering, (May, 1999) vol. 46, No. 5, pp. 548–555.

* cited by examiner

*Primary Examiner*—Kennedy Schaetzle
(74) *Attorney, Agent, or Firm*—Browdy and Neimark, P.L.L.C.

(57) ABSTRACT

An evaluation method that includes:
- recording the values of a physiological signal during a certain measuring period;
- dividing the obtained time series of signal values into individual segments;
- mapping successive subsets of the individual signal values in a segment on associated symbol series according to the criterion of whether a respective signal value increases or decreases as compared to the preceding signal value;
- determining the frequencies of the varying symbol series;
- determining a testing parameter which reflects the frequency ratio, within a segment, of correlated symbol series to anti-correlated symbol series;
- determining the relative difference of the testing parameters of two adjacent segments; and
- comparing the relative difference of two testing parameters with a given threshold as a criterion for the stationarity of the time series of the recorded physiological signal.

11 Claims, 3 Drawing Sheets

EVALUATION METHOD AND APPARATUS FOR DETERMINING THE TIME STATIONARITY OF MEASURED PHYSIOLOGICAL SIGNALS

BACKGROUND OF THE INVENTION

1. Field of the Invention

The invention relates to an evaluation method for determining the time stationarity of measured physiological, in particular cardiologic, signals, which can be implemented preferably on implantable cardiologic devices, such as defibrillators, heart pacemakers or comparable devices.

2. Background Art

For comprehensibility of the present invention, the background must be explained in detail. The most important method of obtaining information on the cardiovascular system resides in recording the ECG by electrodes that are attached to a patient's body surface. Alternatively, a suitable measuring arrangement that includes an implant connected to an electrode may help record an intracardiac ECG or a signal that reflects the course of contraction in an entirely different way, such as intracardiac impedance. As a rule, the morphology of the signal course is evaluated for pathologic processes to be diagnosed or suitable therapeutic measures to be taken.

If any discrete parameters are extracted from the continuous ECG signal, such as the distance of the R wave of the heartbeat at an instant from the R wave of the preceding heartbeat (RR intervals), and if the sequence of values thus produced is outlined in dependence on the number of consecutive heartbeats measured, one will obtain a time series of this cardiac parameter.

It is assumed that in addition to accidental influences, the time series substantially reflects the global regulatory behavior of the cardiovascular system, i.e. the time series, in an abstract manner, gives information on internal transfer functions between components, on latencies of the information transfer between sensors and actuators, or on the working points of the internal transfer functions.

Attempts are made to characterize the status of the cardiovascular system by modeling from time series. This serves various purposes, such as risk stratification or prediction of potentially lethal cardiac events by a defibrillator, or gauging an adaptive frequency cardiac pacemaker. For correct modeling to be ensured, it is necessary to eliminate time series that are influenced by accidental events or during which a patient's condition of physical or psychic stress changes during the period of observation. In the first case, a deterministic model produced from the measurement does not represent the factual condition of the cardiovascular system. In the second case, this condition is not defined at all, owing to a drift or a sudden rise of a parameter of the cardiovascular system. These considerations show that, with a view to obtaining a criterion of stationarity, a selection of certain segments of a time series is a fundamental requirement for modeling and thus for characterizing certain conditions.

So as to be employed in electronic implants, a test for stationarity is required to exhibit, as further decisive criteria, the ability of being automated and the greatest possible simplicity, since the computing capacity is restricted in such implants—at least according to the current state of the art. This is fundamentally due to the fact that as compact as possible computing components must he used which can operate only at an energy supply of limited capacity. As will be explained below, the invention proceeds from these problems.

Regarding the problems posed by the conditions of stationarity upon measurement of any time series, standard tests are known, which are based on a complicated statistical evaluation of the time series and which, as such, do not appear suitable to implementation in implanted cardiologic devices of the current state of processor engineering. However, they will be explained in connection with the invention in order to illustrate the influence of disturbances of stationarity in a time series segment on the evaluation itself. Disturbances of stationarity of a segment can be divided into random and dynamic disturbances. Random disturbances comprise events produced in the heart that are not subject to regulation by the cardiovascular system, such as a temporary atrioventricular block or extrasystoles, i.e. contractions of the ventricle that are not due to sinus node excitation. Random disturbances result from the reception of stimuli from the surroundings, such as sudden noises, but also from inner processes, such as motivations, changes of attention or dreams, Dynamic disturbances result for instance from varying physical and mental stresses over the day that are due to a candidate's activities and go along with varying metabolic demand.

Dynamic disturbances can largely be avoided in physiological experiments. Conventionally, this is achieved by the test conditions being correspondingly prepared, i.e. the candidate is examined in an environment of poor excitation and simultaneously invited to show a passive behavior. However, the examination as such causes multiple psychic processes which can be mastered only by massive drugging. This will interfere with the examination of the regulatory behavior of the cardiovascular system that is affected by the drugging.

Therefore, strictly speaking, preparing test conditions is not possible, and a stationary segment cannot be defined "a priori", which is all the more true for an implant of autonomic operation. In clinical tests, stationary measuring intervals are mostly determined "by inspection" and "a posteriori", i.e., for further evaluation, the experimenter selects, from a given time series, a segment as being stationary during which, in his individual view, the signal seems to have a more uniform course than in the remaining segments. The disadvantages of this way of proceeding reside in the subjectivity of this evaluation method, which is primarily based on the lack of quantitative criteria. Moreover, a range may be defined as stationary that is in fact not stationary, which will render any subsequent evaluations faulty. Finally, any subjective definition of measuring intervals that are assumed to be stationary will make various patients comparable only to a limited degree. Also, by nature, subjective evaluation methods of this type cannot be automated.

For identification of the stationary conditions that are necessary for modeling and thus for general diagnostics, and for elimination of nonstationary measuring segments, a method is required that enables the stationarity to be determined "a posteriori" and that simultaneously obeys to the following criteria:

The method must be objective, it must make available a criterion for the fundamental existence of a stationary condition, and it must be quantifiable, comparable and capable of being automated.

In addition, the method is desired not to be based on pure empirism, but to produce a reference to physiological modifications that accompany nonstationary cardiovascular behavior, for the specificity of the test to be augmented.

The simplest type of a statistic test for stationarity is based on the comparison of empiric distributions in two successive segments. The statistic moments of the distributions are determined and compared by means of so-called "two sample tests". If a significant difference results between the moments of the two distributions, the assumption of stationarity is rejected. This may be a very simple method, but it interprets the cardiovascular system as a purely stochastic system, i.e. as a system having an unlimited number of internal degrees of freedom. Moreover, varying conditions of the cardiovascular system are represented by identical distributions.

Assuming that, apart from external and internal random disturbances, the cardiovascular system obeys to deterministic conditions of development, i.e that the subsequent heartbeat is precisely determined by all the preceding heartbeats, the nonlinear dynamics provide various stationarity tests. Since, however, they are based on the so-called correlation integral, they are very complicated, requiring a well-founded knowledge on a number of unknown parameters and the existence of comparatively long stationary intervals. Moreover, the assumption of a strictly deterministic system as a basis of regulation of the cardiovascular system is definitely as unrealistic as the total randomness thereof. Since the great number of internal degrees of freedom is presumably not entirely coupled, internal system noise is to be expected even when all stochastic disturbances are entirely eliminated.

It is more realistic to assume that correlations play a major role in the cardiovascular system, which are however superposed by internal noise even in the stationary condition. For empirical purposes it is not necessary to specify these components in detail; it is sufficient to find a method for a stationarity test that will take both factors into account. A combination of stochastic behavior with deterministic correlations is grasped by the concept of the fractional Brownian motion (fBm) described in the following.

If the course of a cardiac time series is interpreted as the motion oriented in time of an individual particle that can walk to various places in the direction of the y axis, you will obtain a random walk or a one-dimensional Brownian motion. This motion is equal to the ordinary stochastic Brownian motion of for instance a particle, if the respective step of motion takes place totally independently from all the preceding steps. But if the respective step depends partially on the motion of prior steps, this is called a fractional Brownian motion. In this case, two fundamentally different cases occur. The current step of motion may take place in the direction of the single or of several prior steps or it may be opposite to them. The stronger the one or the other probability is distinguished, the more this will characterize the course of the time series in comparison to the Brownian motion, in which the probability for both directions is identical. The type of this correlation is measured for instance by the Hurst scaling exponent H, which may range between 0.0 and 1.0. A high value corresponds to a very smooth course of the time series, the probability being great that the current step is oriented in the direction of the preceding step. With a low H value, the time series appears "roughened". This is still going to be explained on the basis of a corresponding illustration of simulated time series in the exemplary embodiment (cf. FIG. 1).

In the present context, a verification of measuring-value time series for stationarity proceeds from the assumption that two segments of a time series represent identical conditions of the system when the Hurst scaling exponent thereof has the same value. In this case, the system is assumed to be stationary during both segments. A threshold must be given, below which a difference can be assumed as not yet significant. This threshold is determined empirically or from simulations. Attention must be paid to the fact that the realization of a fractional Brownian motion includes a stochastic component in spite of the correlations and that two time segments can never be distinguished accurately and at a hundred percent sensitivity.

The difficulties, resulting therefrom, in distinguishing various segments are going to be explained in detail in the following description of the exemplary embodiment, taken in conjunction with FIG. 2.

The Hurst scaling exponent may be fundamentally suitable for the evaluation of correlations and thus for a test for stationarity of time series, however the determination of this exponent by known standard methods is complicated, which means that implementation on an implanted cardiologic device cannot be put into practice. Moreover, accurate quantification of the Hurst scaling exponent by standard methods is difficult in particular for shorter time series as they are relevant predominantly in connection with cardiologic measuring values in the case of application in implantable devices.

SUMMARY OF THE INVENTION

Proceeding from the prior art problems, it is an object of the invention to specify an evaluation method that can be implemented on implantable cardiologic devices and which offers a simple way of determining, by restricted computing capacity, the time stationarity of measured cardiologic signals.

This object is attained by an evaluation method comprising the following steps:

recording the values of a cardiologic signal during a certain measuring period;

dividing the obtained time series of signal values into individual segments;

mapping successive subsets of the individual signal values in a segment on associated symbol series according to the criterion of whether a respective signal value increases or decreases as compared to the preceding signal value;

determining the frequency of varying symbol series;

determining a testing parameter which reflects the frequency ratio within a segment of correlated symbol series to anti-correlated symbol series;

determining the relative difference of the testing parameters of two adjacent segments; and comparing the relative difference of two testing parameters with a given threshold as a criterion for the stationarity of the time series of the recorded physiological signal.

The above method can be subsumed under the term "symbolic dynamics" as a keyword. A time series is mapped on a sequence of discrete symbols, with the information included in the time series being compacted. Since the information, under regard, of cardiac time series comprises correlations and anti-correlations, the symbols used here only illustrate the respective directions of the "motion" B(H) that represents for instance the respective RR interval. If B(H)—i.e. the signal value—increases, then the symbol "1" is allotted to the step; if B(H) decreases, the symbol "0" corresponds to this.

Mapping the individual signal values B(H) of a time series on bit words of a defined bit number comprising the elements 0 and 1 preferably corresponds to a function of representation $$B_n(H)=1 \text{ for } B_{n+1}(H)-B_n(H) \geq 0$$

and $$B_n(H)=0 \text{ for } B_{n+1}(H)-B_n(H)<0.$$

In order to examine whether the direction is changed more frequently or whether it is maintained, bit words are formed, having preferably five symbols, such as "01010", which corresponds to a distinct anti-correlation. The frequency of words that correspond to a predominant anti-correlation are related to the frequency of words that represent a correlation. This relation determines a testing parameter, the value of which is compared for two intervals, furnishing a quantitative reference scale.

Realization by the aid of another method that measures stochastic correlations takes place analogously, the difference residing in that the testing parameter has to be suited to the respective method.

In conclusion, the difference between symbolic dynamics and direct computation of H resides in the missing consideration of long range correlations, which are however less relevant given the short segments of the physiologic stationary time series that are to be examined. The property of self-similarity that defines a fractional Brownian motion is not strictly examined either, which is of minor interest for the practical purpose here envisaged. An advantage of symbolic dynamics resides in that extrasystoles are not disproportionately weighted, owing to their height. Therefore there is no need of filtering. Due to the short-long sequence in extrasystoles, a great number of extrasystoles may however lead to the correlation being shifted in the direction of reverse relations between the individual steps of the motion. Further adaptation of the word length on an empiric basis seems conceivable.

Finally, the invention relates to an implantable cardiologic device, in particular a defibrillator or cardiac pacemaker, having an operation control program with the described evaluation method according to the invention implemented.

Further features, details and advantages of the invention will become apparent from the ensuing description of an exemplary embodiment, taken in conjunction with the drawings:

DESCRIPTION OF THE PREFERRED EMBODIMENT

Figure 1:
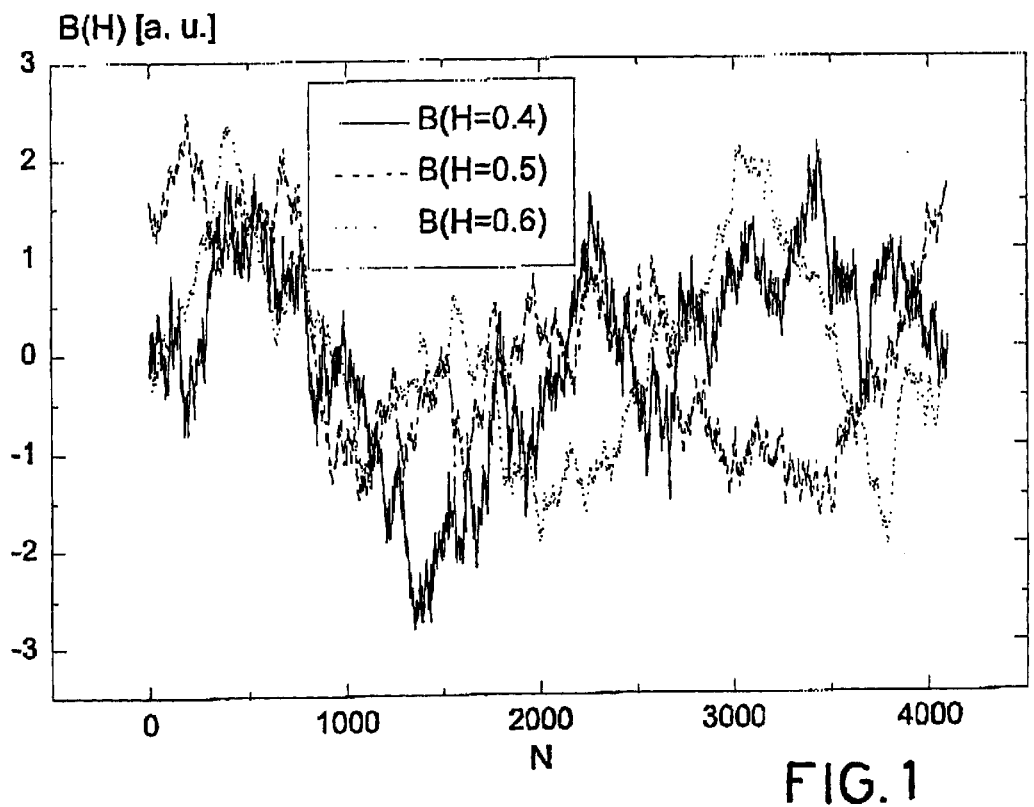
FIG. 1 is a curve diagram of three simulated measuring-value series B(H) in dependence on measuring points N.

FIG. 1 illustrates a simulated time series of the measuring value B(H) in arbitrary units (a.u.) in dependence on simulated measuring points N, the range of which reaches from 0 to 4000. As becomes apparent from the legend of the measuring diagram according to FIG. 1, the curved lines are measuring curves of varying Hurst scaling exponents H, with the solid line reflecting a low exponent of H=0.4, the dashed line a mean exponent of H=0.5, and the dotted line a high scaling exponent of H=0.6. As mentioned, the measuring curves become smoother as the exponent H grows. Corresponding measuring curves will result for instance when the respective duration of the RR interval of the heart is plotted over a corresponding number of measuring points N.

Figure 2:
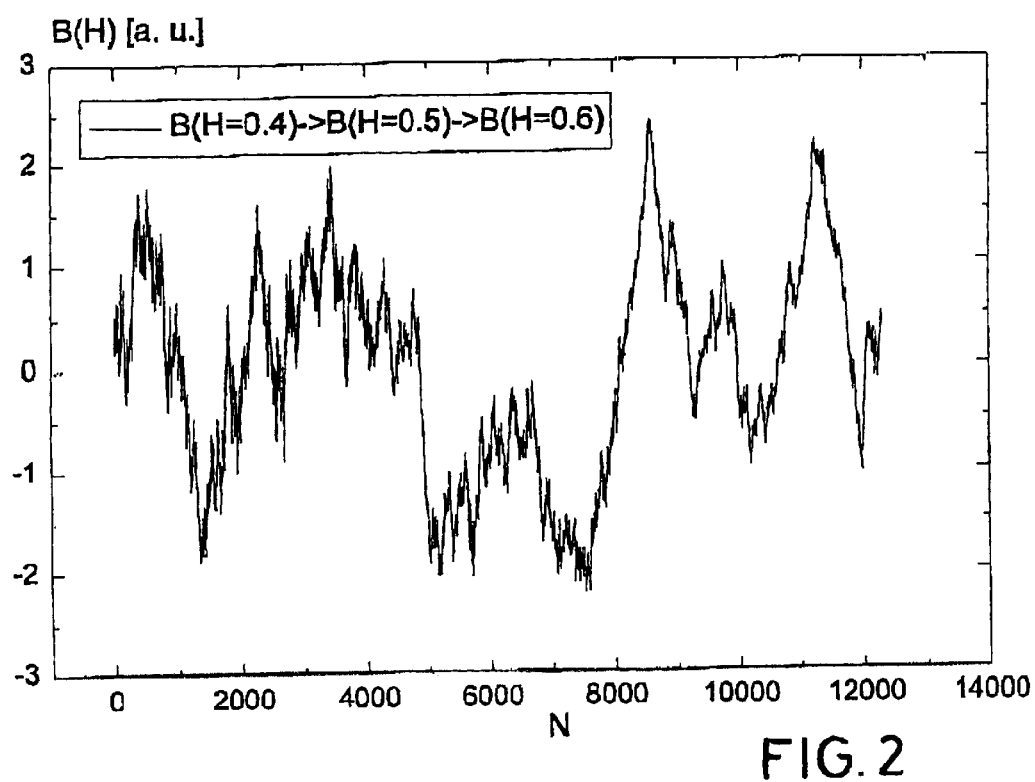
FIG. 2 is a curve diagram of the three measurement curves B(H) according to FIG. 1 in a successive representation with the Hurst scaling exponent H increasing in dependence on the measuring points N.

FIG. 2 illustrates the "successive circuiting" of the three simulation curves seen in FIG. 1 and clarifies the difficulty of distinguishing between varying segments of a time series. By intuition, a certain smoothing of the curve with increasing N can he seen in FIG. 2, which corresponds to the growing Hurst scaling exponent. The transition between the individual segments is however not quantifiable. Assuming nonstationarity due to great leaps of the measuring value B(H), this value would even be diagnosed as faulty at N=5000. Only by computation of the scaling exponent H itself, varying dynamics can be allocated to the three segments.

Referring to FIGS. 2 to 5, the evaluation method according to the invention is going to be explained. The starting point consists in recording the values of a cardiologic signal during a certain measuring period, this meaning that for instance a time series of RR intervals is measured (step 1 in FIG. 3). A diagram of the type seen in FIG. 2 represents this time series to have N=12400 measuring points. It is now the object of the evaluation method to verify the stationarity of the lime series or of certain segments thereof, for this time series or the segments to be made available for further reasonable signal processing so that physiologically reliably conclusions can be derived therefrom for the control of the implant.

Figure 3:
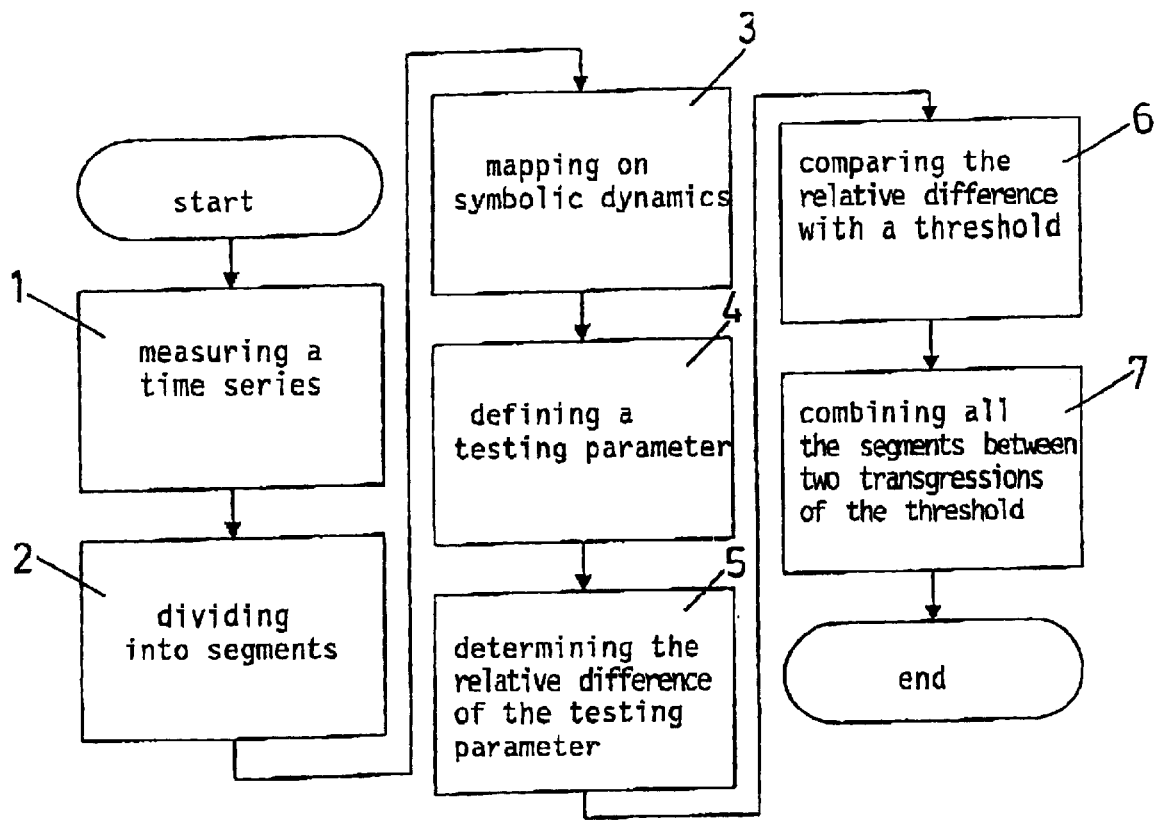
FIG. 3 is a flow chart of the evaluation method according to the invention.

Then the time series is divided into segments of identical length (step 2 in FIG. 3). The length of an individual segment must not be selected too long, because nonstationary intervals within a segment might be overlooked. It must not be selected too short, because otherwise there will not be sufficient significance in determining the result for a testing parameter.

The testing parameter is determined by segments. It is defined as follows by the aid of symbolic dynamics: Subsets of the individual signal values are mapped on a sequence of the symbols "0" and "1", depending on whether the signal value B(H) decreases or increases (step 3 in FIG. 3). This function of representation is characterized as follows:

$$B_n(H)=1 \text{ for } B_{n+1}(H)-B_n(H) \geq 0$$

and $$B_n(H)=0 \text{ for } B_{n+1}(H)-B_n(H)<0.$$

The "letters" of the sequence of symbols are then combined to form a word of five symbols for words to result for instance of the type "01010" or "00000". The frequencies of occurrence of certain words in a segment are counted, for example P("01010") or P("00000").

The sum of word frequencies of equidirectional correlation ($\Sigma P_{corr}$), such as P("00000")+P("11111"), is related to the sum of word frequencies of opposite correlation ($\Sigma P_{anticorr}$), such as P("10101")+P("01010").

Figure 4:
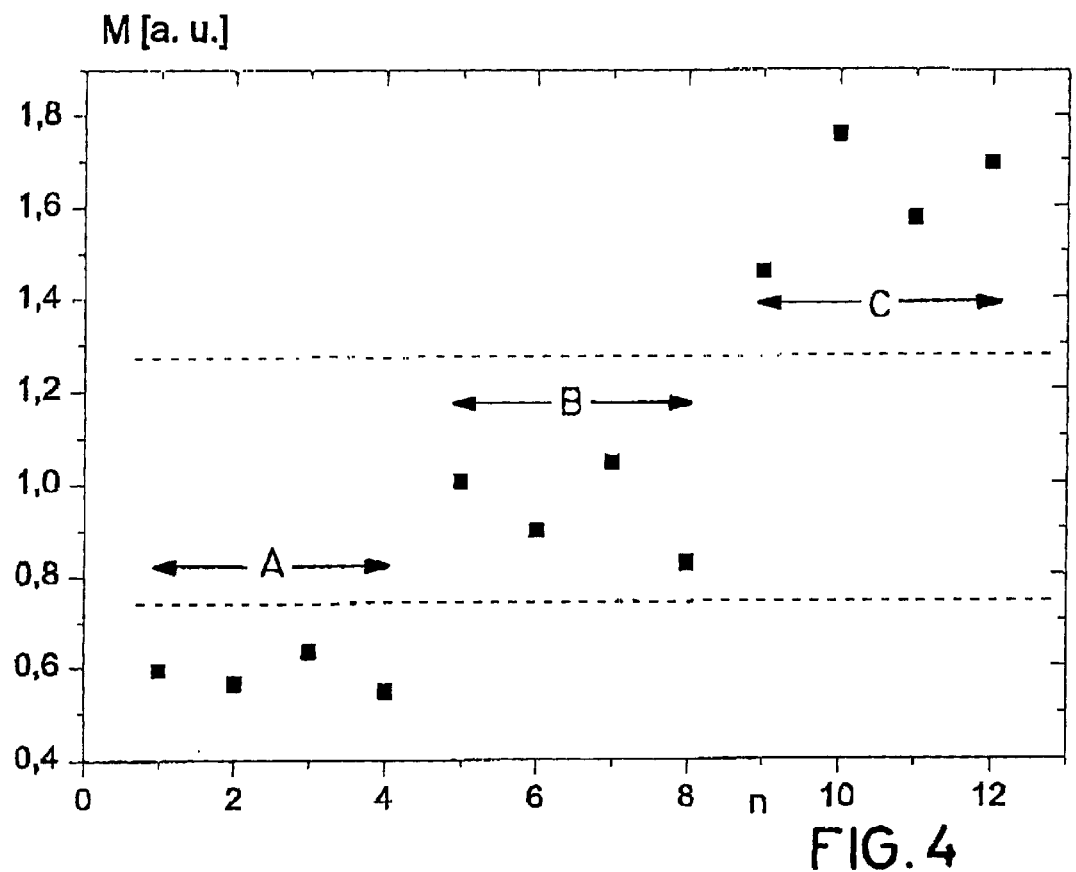
FIG. 4 is an evaluation diagram of the testing parameter M in dependence on a segment number n.

If the time series of FIG. 2 (total length 12400) is divided into segments of the length 1000, and if the quotient $$M = \left(\sum P_{corr}\right) / \left(\sum P_{anticorr}\right) \text{ and}$$

$$M = \frac{P(00000) + P(00001) + P(01111) + P(10000) + P(11110) + P(11111)}{P(10101) + P(00101) + P(00000) + P(01011) + P(01101) + P(01101) + P(10010) + P(10100)}$$

is defined as a testing parameter (step 4 in FIG. 3)—with the use of individual words determined empirically as is the segment length of cardiac time series—this will give the interrelationship seen in FIG. 4. The results of the testing parameters M for the individual segments of the time series of FIG. 2 are plotted over the number n of the segment. Clearly, three segments A, B and C (FIG. 4) exist in the time series, having, among each other, disjunctive quantities of values of the testing parameter. The further proceeding of an automated test can be derived from this.

It is then checked whether the testing parameter of two adjacent segments differ beyond a certain extent. To this end, the relative difference Δ is determined as a dimension figure (step 5 in FIG. 3):

$$\Delta = \frac{M_{i+1} - M_i}{M_i} \times 100\%.$$

Figure 5:
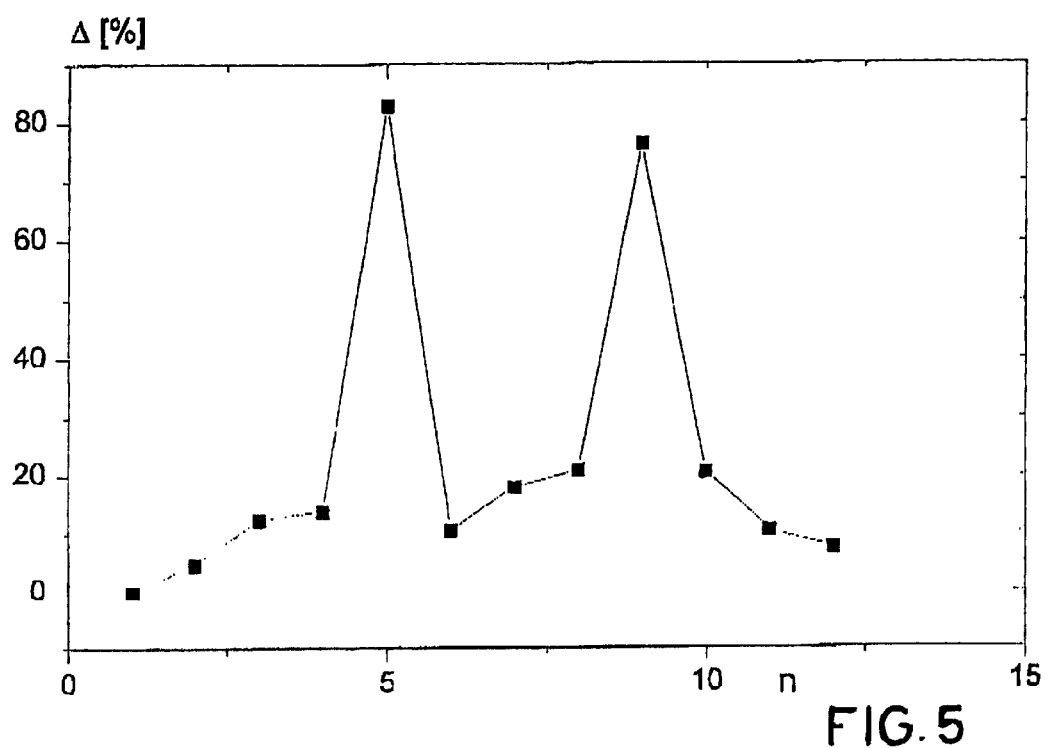
FIG. 5 is an evaluation diagram of the relative difference Δ in dependence on the segment number n.

For the time series of FIG. 2, the dimension figure Δ is plotted over the number of the pair of segments n in FIG. 5.

FIG. 5 shows that it is sufficient to define another threshold criterion in order to decide whether pairs of segments have the same or varying dynamics. This threshold is defined empirically for cardiac time series. Regarding the example chosen, a threshold of for instance 50% can easily be given for the relative difference of the testing parameter M, below which a pair of segments is considered stationary. A pair of segments for which the relative difference of the testing parameter exceeds 50% is rejected (step 6 in FIG. 3). Regarding FIG. 5, attention is drawn to the fact that the segments of varying dynamics differ only by ΔH=0.1 so that the evaluation method obviously reacts very sensitively. in the case of low sensitivity, the testing parameter may additionally be evaluated directly by analogy to FIG. 4.

For further evaluation and modeling of the time series of FIG. 2, the course of the dimension figure Δ seen in FIG. 5 shows that the segments n=1–4, n=5–8 and n=9–12 may be combined for further evaluations and modeling (step 7 in FIG. 3). A single modeling job must however not comprise segments that are in varying ranges of the three ranges found.

Attention must also be paid to the fact that the stationarity is global for the respective pair of segments, i.e. it cannot be excluded that nonstationary ranges occur within one of the segments if the length of the segment has been selected too long. This can be prevented by stepwise decrease of the length of the segment. Further variations of the method are conceivable, such as variability of the width of a segment or sliding segments.

What is claimed is:

1. An evaluation method, for determination of time stationarity of measured physiological signals, in particular cardiologic signals, comprising the following steps:

recording values of a physiological signal during a certain measuring period for obtaining a time series of signal values;

dividing the obtained time series of signal values into individual segments;

mapping successive subsets of the individual signal values in a segment on associated symbol series according to a criterion of whether a respective signal value increases or decreases as compared to a preceding signal value;

determining frequencies of the varying symbol series;

determining a testing parameter which reflects a frequency ratio, within a segment, of symbol series of varying correlation stages;

determining a relative difference of the testing parameters of two adjacent segments; and comparing the relative difference of two testing parameters with a given threshold as a criterion for the stationarity of the time series of the recorded physiological signal.

2. A method according to claim 1, wherein a respective duration of an RR interval of the heart is recorded as a physiological signal.

3. A method according to claim 1, wherein individual signal values B(H) of the time series are mapped as respective symbol series on bit words of a defined bit number comprising symbol elements 0 and 1 by a function of representation $$B_n(H)=1 \text{ for } B_{n+1}(H)-B_n(H)\geq 0$$

and $$B_n(H)=0 \text{ for } B_{n+1}(H)-B_n(H)<0.$$

4. A method according to claim 3, wherein each bit word includes five symbol elements.

5. A method according to claim 3, wherein a sum of bit word frequencies ($P_{corr}$) of equidirectional correlations is related to a sum of bit word frequencies ($P_{anticorr}$) of opposite correlations as a testing parameter (M) by an equation $$M=(\Sigma P_{corr})/(\Sigma P_{anticorr}).$$

6. A method according to claim 5, wherein a relative difference (Δ) of the testing parameters (M) of two adjacent segments is determined by a relation $$\Delta=(M_{i+1}-M_i)/M_i\times 100\%.$$

7. A method according to claim 6, wherein the given threshold for the time series stationarity is in the range of 50%.

8. A method according to claim 1, wherein coherent segments complying with the criterion of stationarity are used as a basis for further cardiologic evaluation of the recorded cardiologic signals.

9. The method of claim 1, wherein said method is performed on an implantable cardiologic device.

10. The method of claim 1, wherein the symbol series of varying correlation stages are correlated symbol series to anticorrelated symbol series.

11. An implantable cardiologic device, in particular a defibrillator or cardiac pacemaker, including a storage medium that contains an operation control program thereon which implements an evaluation method for determination of time stationarity of cardiologic signals measured by the implantable cardiologic device comprising the following steps:

recording values of a physiological signal during a certain measuring period for obtaining a time series of signal values;

dividing the obtained time series of signal values into individual segments;

mapping successive subsets of the individual signal values in a segment on associated symbol series according to a criterion of whether a respective signal value increases or decreases as compared to a preceding signal value;

determining frequencies of the varying symbol series;

determining a testing parameter which reflects a frequency ratio, within a segment, of symbol series of varying correlation stages, in particular of correlated symbol series to anticorrelated symbol series;

determining a relative difference of the testing parameters of two adjacent segments; and comparing the relative difference of two testing parameters with a given threshold as a criterion for the stationarity of the time series of the recorded cardiologic signal.

* * * * *